United States Patent [19]

Anantaneni et al.

[11] Patent Number: 5,118,652
[45] Date of Patent: Jun. 2, 1992

[54] FERRIC PHOSPHATE CATALYST FOR USE IN THE MANUFACTURE OF ALKYL GLYOXYLATE

[75] Inventors: Prakasa R. Anantaneni, Manchester; Tao P. Li, Chesterfield, both of Mo.

[73] Assignee: Monsanto Company, St. Louis, Mo.

[21] Appl. No.: 585,577

[22] Filed: Sep. 19, 1990

Related U.S. Application Data

[60] Continuation-in-part of Ser. No. 417,396, Oct. 5, 1989, abandoned, which is a division of Ser. No. 230,289, Aug. 9, 1988, Pat. No. 4,900,864, which is a division of Ser. No. 156,874, Feb. 18, 1988, Pat. No. 4,820,385.

[51] Int. Cl.$^5$ .......................... B01J 27/85; B01J 27/18
[52] U.S. Cl. ...................................... 502/213; 502/208
[58] Field of Search ................ 502/208, 355, 338, 213

[56] References Cited

U.S. PATENT DOCUMENTS

| | | | |
|---|---|---|---|
| 3,398,100 | 8/1968 | Christmann et al. | 502/208 |
| 3,555,105 | 1/1971 | Nolan et al. | 502/208 |
| 3,974,233 | 8/1976 | Lawrenson | 502/208 |
| 4,021,370 | 5/1977 | Harris et al. | 502/210 |
| 4,080,311 | 3/1978 | Kehl | 502/208 |
| 4,827,037 | 5/1989 | Doumaux, Jr. | 502/208 |

*Primary Examiner*—Anthony McFarlane
*Attorney, Agent, or Firm*—R. C. Loyer

[57] ABSTRACT

A process of this invention for producing glyoxylate esters is carried out by contacting a with a catalyst comprising ferric phosphate on an alumina supportfeed composition comprising an oxygen containing gas and a vaporized lower alkyl ester of glycolic acid. The process of the invention can be carried out as either a fixed bed or a fluid bed operation.

9 Claims, 1 Drawing Sheet

FERRIC PHOSPHATE CATALYST FOR USE IN THE MANUFACTURE OF ALKYL GLYOXYLATE

This application is a continuation-in-part of application Ser. No. 417,396 filed Oct. 5, 1989, now abandoned, which application is a division of application Ser. No. 230,289 filed Aug. 9, 1988 now U.S. Pat. No. 4,900,864, which is a division of Ser. No. 07/156,874 filed Feb. 18, 1988, now U.S. Pat. No. 4,820,385.

This invention relates to a process for the manufacture of glyoxylic acid esters by oxidation of the corresponding esters of glycolic acid and, more Particularly, to an improved glycolic acid ester oxidation process providing high levels of selectivity and conversion in which an improved catalyst comprising ferric phosphate supported on alumina is employed.

BACKGROUND OF THE INVENTION

Polyacetal carboxylates have been demonstrated to be useful as builders in detergent formulations. Crutchfield U.S. Pat. No. 4,144,226 describes the preparation of polyacetal carboxylates by polymerization of an ester of glyoxylic acid, preferably methyl glyoxylate. The glyoxylic acid ester monomer may be prepared by vapor phase oxidation of the corresponding ester of glycolic acid. This process can be represented as follows:

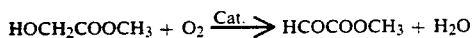

$$HOCH_2COOCH_3 + O_2 \xrightarrow{Cat.} HCOCOOCH_3 + H_2O$$

Various catalysts have been proposed for use in this vapor phase process including silver as well as a catalyst composed of one or more of vanadium, molybdenum, silver, and copper in combination with a promoter such as tin, antimony, bismuth, or an element of Group IA or Group IIA of the Periodic Table. See U.S. Pat. No. 4,340,748. While the selectivity and conversion obtained with silver catalysts are good, an improvement in the level of conversion, and especially conversion and selectivity, is desirable.

SUMMARY OF THE INVENTION

Accordingly, it is an object of this invention to provide an improved catalyst for the vapor phase oxidation of glycolic acid esters consisting essentially of ferric phosphate supported on alumina. A further object is to provide an improved catalyst of the type described whereby very high conversions of glycolate ester can be obtained. In particular, it is an object to provide an improved catalyst that can be used to achieve both high conversions of glycolate ester and high selectivity to the corresponding glyoxylate ester.

An additional object is to provide an improved process for the manufacture of a glyoxylate ester by the vapor phase oxidation of a glycolate ester.

The process of this invention for producing glyoxylate esters is carried out by contacting a catalyst consisting essentially of ferric phosphate on an alumina support with a feed composition comprising an oxygen containing gas and a vaporized lower alkyl ester of glycolic acid. Those skilled in the art are well aware of the various systems available for the practice of vapor phase reactions as well as how to design and operate those systems. Thus, for example, the process of the invention can be carried out as either a fixed bed or a fluid bed operation.

In accordance with this invention there provided a novel catalyst useful in a process for the vapor phase oxidation of glycolic acid esters comprising a support material selected from the group consisting of alumina and silica containing alumina having as the only added metal catalyst ferric phosphate. The catalyst is a calcined residue prepared as further described below. A particularly preferred form of the catalyst is one wherein the support material has a surface area between about 0.02 m²/g and about 5 m²/g. Accordingly, the term "consisting essentially of" as employed herein means that ferric phosphate is employed as the only added metal catalyst to the support material.

Other objects and features will be in part apparent and in part pointed out hereinafter.

DETAILED DESCRIPTION OF THE INVENTION

Figure 1:
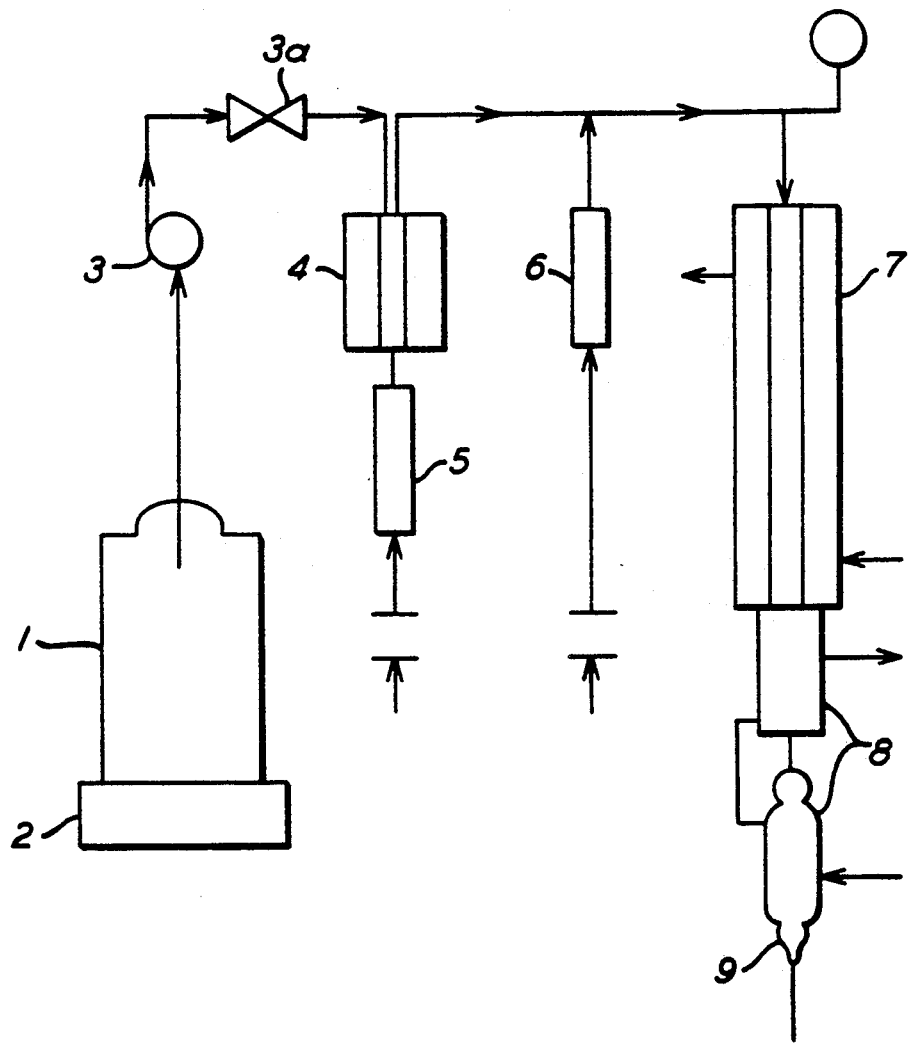
FIG. 1 is a schematic drawing of the fixed bed reactor system used in carrying out the process of the invention.

The catalyst of this invention can conveniently be prepared by first forming an aqueous solution of ferric ions ($Fe^{+++}$), conveniently done by adding a suitable ferric salt to a vessel containing water at room temperature, and then adding an essentially stoichiometric amount of phosphoric acid, that is, an amount of phosphoric acid sufficient to utilize all of the ferric ions present. Conveniently, 85% Phosphoric acid is used but other concentrations can also be used.

The alumina support material is then impregnated with the ferric salt/phosphoric acid solution by mixing the two together at room temperature. To facilitate handling the thus impregnated alumina particles are usually then dried, at about 110° C., to provide a precatalyst. The relative proportions of impregnation solution and alumina support material are selected so as to ultimately provide the desired concentration of ferric phosphate on the support material. Depending upon the concentrations of ingredients in the impregnation solution, and the ferric phosphate concentration desired, more than one impregnation step may be required. The precise concentration of ferric phosphate is not critical in the sense of whether the process is or is not operational. For most operations, however, concentrations of ferric phosphate on the alumina support material will be in the range of about 1–20%, but preferably, in order to obtain good selectivity, about 11–14%. The level of active catalyst does not seem to have a dramatic effect on selectivity, but in combination with the other controllable variables, provides an additional means of controlling the process. It is generally accepted in the catalytic art that, where an alumina support material is one high in silica, it is often advantageous to incorporate a potassium salt, e.g. potassium nitrate, to reduce the acidic properties of such a support, especially where the material to be oxidized is relatively sensitive to hydrolysis under acidic conditions. In the present process the addition of small amounts of a potassium salt, such as potassium nitrate, may be added to the aqueous medium along with the ferric salt.

After the precatalyst is prepared it is subjected to a calcining operation wherein the pre-catalyst is heated in air. The air can be relatively static or an air sweep can be used. An air swept furnace, e.g. a muffle furnace, has been found useful for the calcining operation. It has been found that for calcining, temperatures of the order of from about 400° C. to about 800° C. for from about 3 to about 6 hours give satisfactory results. Calcining at about 500°-600° C. for about 3-5 hours has been found to provide good results and is preferred. The catalysts may be used immediately or stored until needed. No special conditions of storage are required.

As a source of ferric ions it is desirable to employ a ferric salt that has a level of solubility in water which will allow the preparation of catalysts wherein the concentration of ferric phosphate on the alumina support material can be easily increased or decreased as desired. Representative ferric salts are ferric nitrate sextahydrate, ferric nitrate nonahydrate, ferric formate, ferric citrate, ferric bromide and ferric chloride.

The alumina support material useful in preparing the catalysts of this invention is commercially available, usually as spheres having an average diameter in the range of from about 1/16 inch to about ¼ inch. Alumina support material of other sizes and shapes is also available and useful but a generally spherical shape is described herein to illustrate the invention. Preferably the alumina is in the $\alpha$-alumina form.

The surface area of the alumina will generally be in the range of from about 0.02 $m^2$/gram to as high as 45 $m^2$/gram. Preferably the surface area will be less than about 5 $m^2$/gram. In addition, the alumina material utilized may contain silica in amounts varying from 30% to less than 1% by weight. Preferably, alumina of lower silica content is employed, that is, an alumina containing about 20% or less, more preferably about 12% or less by weight silica. The selection of the specific alumina material to be employed as the support material for the catalysts of this invention will of course be guided by such factors as commercial availability of the alumina material and oxidation reactor system design. In the fixed bed oxidation system described herein, it has been found that the average particle size of the alumina support material has an effect upon conversion and selectivity. In general, particles having an average size of more than about 3/16 inch (4.7 mm) caused lower conversions and lower selectivities. However, with larger scale equipment, particles of an average diameter of about ¼ inch (6 mm) or larger can be used. A particle size of between about 0.125 inches (3 mm) and 0.07 inches (1.8 mm), for example is preferred for the oxidation of methyl glycolate in the equipment used in developing the instant process. A major criteria for the selection of particle size is to employ a support material which provides a minimum pressure drop and avoids channeling within the catalyst bed. Generally a ratio of reactor diameter to the average diameter of the support material of about 6 to 1 minimum, is satisfactory. A catalyst support material with too high of a surface area gives low selectivity.

In any event an alumina support material having physical properties within the parameters set forth above will be found to be useful in the practice of this invention. Examples of commercially available alumina support materials include various Norton Company products which are $\alpha$-alumina materials in the form of spheres with an average size of about 3/16 inch (4.7 mm) containing less than about 20% by weight silica. Examples include the Norton products designated as SA5205, which has a surface area of less than 0.05 $m^2$/gram; SA3235, which has a surface area of 8-16 $m^2$/g ; SA3232, which has a surface area of 25-35 $m^2$/g.; and SA5202, which has a surface area of 0.7-1.3 $m^2$/g. Other examples of commercially available $\alpha$-alumina materials include Carborundum Company SAHO which comes as 3/16 inch (4.7 mm) spheres with a surface area of less than 1 $m^2$/g.

In order to practice the process of this invention a selected catalyst of this invention is loaded into a suitable reactor. FIG. 1 is a schematic drawing of the fixed bed reactor system used in carrying out the process of the invention. In this system glycolate ester feed from vessel 1, which is placed on a balance or scale 2, is delivered by pump 3 to vaporizer 4, comprised of a ½ inch (12.7 mm) tube 8 inches (203 mm) long within a 4 inch × 8 inch (102 mm × 203 mm) insulated and heated aluminum block, where it is mixed with air which has been heated to about 150° C. by heater 5, vaporized, and passed to reactor 7. Valve 3a is placed in the feed line down stream from pump 3 to prevent backflow of gas. Reactor 7 is comprised of a jacketed 316 stainless steel tube 1 inch (25.4 mm) in diameter and 14 inches (355 mm) long. In those cases where an inert gas diluent, preferably nitrogen, is added to the process (as described below), that gas, heated by heater 6 to about 150° C., is added to the vaporized mixture of air and glycolate ester and the combined mixture fed to the reactor. In the reactor, glycolate ester is converted to the corresponding glyoxylate ester and other products. The glyoxylate ester is then cooled by condensers 8 and collected in receiver 9, along with other condensables formed in the process. These other condensables include acidic materials such as formic acid, plus water and alkanol.

More specifically the process of the invention comprises passing an alkyl glycolate through a vaporization zone, wherein the glycolate is mixed with a heated source of oxygen, preferably air, and vaporized to form a reaction mixture, and then passing the reaction mixture through a reaction zone containing a catalyst consisting essentially of ferric phosphate on an alumina support to provide a product comprising an alkyl glyoxylate.

Before the catalysts of this invention are put into service it is preferable to subject them to a conditioning or break in operation in order to maximize their performance. Conditioning is accomplished, preferably after the catalyst is installed in a reactor, by contacting the catalyst with a heated gaseous stream comprising a mixture of alkyl glycolate and air, or other oxygen source. Preferably an inert diluent gas is also added to the feed stream which assists in cooling the reactor (maintaining catalyst temperature), minimizing over oxidation and shortening the break in time, as well as providing means for controlling the concentration of oxygen and alkyl glycolate in the feed.

The precise conditions to be used for the conditioning operation depend upon various factors, such as the ester to be oxidized and its concentration in the feed to the catalyst, the alumina support material selected, reactor design, and time and temperature conditions. In general, conditioning of the catalyst is accomplished by first passing a mixture of air or other oxygen containing gas, glycolate and, preferably, inert gas diluent, which mixture has been heated to a temperature of about 125°-165° C., over the catalyst. When using the apparatus of FIG. 1, a heat transfer fluid (temperature of about 300° C.) is initially circulated through the jacket of reactor 7 to bring the catalyst up to the desired temperature. After the initial heat-up of the catalyst, usually over a period of 2 to 3 hours, alkyl glycolate is introduced into the gas feed to the reactor at a relatively low concentration, of the order of 3% to about 5% by volume, and then gradually increased over a period of 4 to 6 hours, to concentrations of the order of 20% or less, preferably about 7-11%. It has been found that conditioning for a few hours, for example from 4 to 6 hours, may be enough or that times as long as 150-200 hours may be needed while still maintaining the proper balance between minimizing the time required for conditioning and preventing damage to the catalyst. The selection of the amount of time for conditioning will ultimately depend upon the feed concentration, catalyst volume and reactor configuration.

During catalyst break in the mole ratio of $O_2$/glycolate should be maintained at about 0.8 to about 1 2, preferably about 1. While the $O_2$/glycolate ratio can be altered outside this range little effect has been noted on the time required for break in or upon catalyst performance. For best results the break in period should be a continuous period; however, interruptions in conditioning the catalyst do not render the catalyst inoperative but do prolong the conditioning period and can cause decreased catalyst Performance. During the conditioning period the temperature in the catalyst bed should be maintained, by cooling or heating the reactor if necessary, at about 280° C. to about 320° C., preferably about 300° C. or slightly below.

Throughout the conditioning operation as well as during normal operations it may be necessary to add or remove heat from the reactor in order to maintain the desired temperatures. Accordingly, the reactor selected should be provided with the necessary means to provide temperature control of the catalyst bed.

It has been found, for example, that for the oxidation of methyl glycolate to methyl glyoxylate using a catalyst containing about 12-13% ferric phosphate, that the catalyst can be satisfactorily conditioned by continuously passing a heated (about 150° C.) mixture of methyl glycolate, air and nitrogen, containing at least about 3%, up to about 10%, preferably in the range of about 7-8%, of the glycolate, having an oxygen to glycolate mole ratio of about 1.08, and containing sufficient nitrogen to maintain the desired $O_2$/glycolate ratio, over the catalyst in a fixed bed reactor, while maintaining the catalyst bed at a temperature of about 300° C. or slightly less, for a continuous period of from about 150-200 hours. Under those conditions a catalyst is provided which gives high conversion with very high selectivity. Following break in, little change in catalyst performance is noted for as long as 1200 hours of operation.

In operating the process of this invention, there are a number of variables which can be controlled so as to achieve a desired result, such as high selectivity, high levels of conversion or, as in the preferred process of this invention, a combination of both high selectivity and high conversion. These variables, in addition to catalyst level and the catalyst support surface area as described above, include glycolate ester concentration, $O_2$/glycolate ester mole ratio (a measure of oxygen concentration in the feed), and catalyst operating temperature.

It has also been found that the level of condensable acidic materials in the glyoxylate ester produced in the process can be decreased by alkanol addition to the feed, using a hybrid catalyst system comprising the catalyst of this invention and a silver catalyst of the prior art, by post treatment of the glyoxylate ester with an ion exchange resin or a combination thereof. Dilution of the glycolate ester feed with an inert gas also contributes to lowering the level of acidic materials produced.

Following the conditioning period the glycolate ester concentration may be increased for long term operation above the concentration used during catalyst break in but is usually about the same as the final concentration selected at the end of the conditioning period. However, if the concentration is to be increased, the rate of increase in concentration of glycolate in the feed to the reactor is selected so as to achieve target operating conditions as rapidly as possible without damaging the catalyst. That rate can be determined experimentally for a given reaction system by maintaining the reactor bed temperature at the desired point. In practice the concentration of glycolate can be increased either by the addition of more glycolate to the feed stream or by slowly decreasing the diluent gas concentration, if one was used, or a combination thereof. However, when operating at the higher levels of glycolate ester concentration, there is a tendency for the catalyst to be reduced causing a rapid decrease in selectivity. Under typical operating conditions the glycolate concentration in the feed to the reactor is from about 3% to about 20% by volume, preferably about 4% to about 11%, and the mole ratio of oxygen to glycolate is in the range of about 0.8 to about 6, preferably about 1 to about 1.2. If the feed mixture is provided by mixing glycolate ester vapor with air only, and if the mole ratio of 02 to glycolate is maintained at about 1, for example, the concentration of glycolate will be about 18-19%, making it difficult to maintain the catalyst bed temperature at desirable levels. If the bed temperature is too high in the presence of high concentrations of glycolate the catalyst can be severely damaged.

However, the glycolate concentration can be adjusted by adding an inert diluent gas to the feed to the reactor or increasing the ratio of oxygen containing gas to glycolate. It is preferred to employ an inert diluent gas, preferably one also preheated to about 150° C., as a means of controlling the glycolate concentration. As used herein, inert gas refers to any gaseous material which is unchanged under the conditions in the reactor. Typical examples are carbon dioxide, nitrogen, helium and off-gas from the reactor. When an inert diluent gas is employed the amount of such gas will generally be that needed to provide from about 3.5% to about 19% $O_2$ in the feed stream. If air is the oxygen source, for example, nitrogen, in addition to that contained in the air, is added to provide the desired $O_2$ concentration.

During normal operation, that is, once the catalyst is conditioned, conversion increases with increasing reactor temperature (that is, catalyst bed temperature) which in turn can be caused, for example, by increasing the glycolate concentration. Accordingly, the reactor temperature is controlled, for example by the use of an appropriate heat transfer medium circulated through jacketing on the reactor, so as to avoid high temperature damage to the catalyst. Of course, as described herein, the reactor temperature can be controlled by other means, such as by the use of lower glycolate concentration, the addition of increased amounts of oxygen containing gas or the addition of diluent gas. Operating temperatures ranging from about 250° C. to about 400° C. have been found to be useful, but the preferred range is from about 275° C. to about 325° C.. Higher temperatures promote poor Selectivity and increase the amount of by-products formed.

With respect to the oxygen concentration in the feed it has been found that a concentration of from about 3% to about 20% by volume is useful, but that in order to avoid difficult to control operations, from about 4% to about 11% should be used to ensure better control of the process and provide longer catalyst life. At increased $O_2$/glycolate ester mole ratios the temperature of the reaction increases and over oxidized products are more readily formed.

For example, in the oxidation of methyl glycolate using air as the source of oxygen and additional nitrogen as diluent gas, it has been found that an $O_2$/glycolate mole ratio of between about 0.8 and about 6, preferably about 1 to about 1.2, with an air to nitrogen ratio by volume of about 1:3 provides a glycolate concentration of about 5%, which is well conditions high levels of selectivity and conversion are realized. On the other hand, if nitrogen or other inert gas is not utilized and increased amounts of air are used in order to maintain methyl glycolate concentration within the preferred range, the resulting higher $O_2$/glycolate concentration adversely affects selectivity and there is an increase in acidic by-products.

While the formation of acidic by-products in the crude alkyl glyoxylate can be controlled by adjustment of the several variables discussed above, as taught herein, their formation cannot be eliminated. For many uses of the glyoxylate esters elimination of acidic materials in the crude product from the oxidation reaction is not necessary. Moreover, later refining provides a means of reducing the level of such materials to within acceptable limits. On the other hand, where there is a requirement for low levels of acidic by-products in the crude glyoxylate so that later refining of the crude will provide an alkyl glyoxylate of high purity, several optional steps are available within the scope of the present invention, which are capable of providing a crude glyoxylate ester having quite low levels of acidic materials, of the order of 1% or lower.

As discussed above, the addition of an inert diluent gas to the feed to the reactor provides a means of controlling various operating conditions, such as reactor temperature, oxygen concentration and glycolate concentration. In addition, the use of such a gas also serves to reduce the amount of acidic by-products formed. For example, it has been found that in the air oxidation of methyl glycolate the addition of nitrogen in a ratio of 3 parts nitrogen to 1 part air provides, under various operating conditions, a reduction in acidic by-products of up to 30-35%.

A further reduction in the level of acidic by-products can be obtained by adding to the feed to the reactor, in addition to inert diluent gas, an alkanol in which the alkyl moiety is the same as the alkyl moiety of the alkyl glycolate. For example, methanol would be used with methyl glycolate and butanol would be used with butyl glycolate. Furthermore, the addition of an alkanol has been found to improve selectivity. The preferred amount of alkanol to be used will vary, depending upon the selection of the operating conditions and glycolate to be oxidized, but an amount in the range of about 5-10% by weight of glycolate feed provides a significant benefit, but an amount up to 20% can be used. It has been found, for example, that by the addition of about 10% by weight methanol, based on glycolate, to a feed comprising about 4.6% methyl glycolate, 5% oxygen and 90% nitrogen, that an additional reduction in acidic impurities of up to about 53% (a net reduction from using a combination of nitrogen and methanol of about 69%) was obtained. Under the same operating conditions increasing the amount of methanol to about 20% provided a further slight decrease in acidic impurities.

A still further method for reducing the concentration of acidic materials in the crude glyoxylate is to use a dual catalyst comprising the ferric phosphate catalyst of this invention in combination with a silver catalyst. By combination is meant that the reaction mixture first contacts a catalyst comprising the ferric phosphate catalyst of the invention and then contacts a silver catalyst. In a reaction system employing a fixed bed reactor this is readily accomplished by packing both catalysts in the same reactor in a manner such that the feed stream firsts contacts the ferric phosphate catalyst. The amount of silver catalyst used should be in the range of 8-12% of the amount of catalyst of this invention, preferably about 10%. An example of a useful silver catalyst is a product sold by Engelhard Industries in the form of silver crystals, referred to as silver needles, in a mesh size of 16 x 30, containing 99.998% pure silver. Utilizing such an arrangement for the oxidation of methyl glycolate with air, in which nitrogen was added to the feed, it has been found that acidic impurities could be reduced to a level of about 1% by weight.

Additionally a further reduction in the amount of acidic materials in the glyoxylate product can be obtained by treatment of the glyoxylate with an ion exchange resin. Typically the glyoxylate can be passed through a column packed with the selected resin, to provide acid levels as low as about 0.1%. The ion exchange resin selected should be one capable of absorbing the acidic materials present. The selection of a particular resin is well within the skill of the art. Resins found to be useful include Amberlite IRA 93 and Amberlite IRA 45, which are basic ion exchange resins sold by the Rohm and Haas Company.

Initially a series of experiments were performed in which methyl glycolate was oxidized in the vapor phase in a fluidized bed reactor using a ferric phosphate on alumina catalyst of the invention. The reactor system was set up similar to the fixed bed system except that the catalyst was in the form of particles in the range of about 38-125 microns. Glycolate ester was metered to a packed evaporator tube placed in a heated and insulated aluminum block. A portion of the air was passed through the vaporizer and the remainder passed through a separate heated airline. Glycolate ester feed vapors mixed with air was passed through the catalyst bed which was placed in a heated sand bath. Product was recovered by cooling the exit vapors in an ice trap. For these experiments a supported catalyst was prepared as described below.

EXPERIMENT A

Ferric nitrate nonahydrate (229.5 grams) and 40 ml of water were mixed in a suitable vessel. The resulting solution was dark brown in color. 68.0 grams of 85% phosphoric acid was then added to produce a light colored clear solution having a volume of 235 ml. 200 grams of $\alpha$-alumina (Norton Company 06948, particle size 38-125 microns, surface area 0.15 m²/g.) were then impregnated using 130 ml of the previously Prepared solution by mixing the alumina and solution together in a suitable flask. Excess water was then removed, by repeatedly subjecting the flask to vacuum and then releasing the vacuum, to provide a precatalyst. The impregnated alumina was then dried in a vacuum oven at 105° C. overnight to provide a precatalyst which was then calcined at 550° C. for two hours. The catalyst contained 19% $Fe_3PO_4$. The catalyst was then charged to the reactor described above. A summary of those experiments and the results obtained are set forth in Table 1 below.

TABLE 1

Methyl Glycolate Oxidation in a Fluidized Bed Reactor

|  | Exp. No. | | | |
| --- | --- | --- | --- | --- |
|  | 1 | 2 | 3 | 4 |
| Catalyst amount grams (g) | 31 | 31 | 31 | 31 |
| Feed Rate (grams/min) | 0.21 | 0.21 | 0.21 | 0.21 |
| Air Flow (SCCH)* | 300 | 350 | 350 | 350 |
| $O_2$/glyc. mole ratio | 1.14 | 1.34 | 1.34 | 1.34 |
| $O_2$ in the mixture (vol. %) | 17.86 | 18.28 | 18.28 | 18.28 |
| Glycolate in the mixture (vol. %) | 14.95 | 12.95 | 12.95 | 12.95 |
| Wt. Hrly. space velocity | 0.41 | 0.41 | 0.41 | 0.41 |
| Contact Time (sec.) | 2.50 | 1.88 | 1.95 | 2.03 |
| Vaporizer Temp (°C.) | 160 | 160 | 160 | 160 |
| Reactor Temp (°C.) | 300 | 400 | 375 | 350 |
| Product Recovery (wt. %) | 90.04 | 73.07 | 66.00 | 67.17 |
| Conversion (Wt. %) | 57.60 | 99.67 | 99.43 | 98.92 |
| Selectivity (Wt. %) | 48.66 | 40.71 | 37.00 | 27.06 |

*SCCH = standard cubic cm/hr

As is evident from these results the catalysts of this invention are capable of providing high conversions, on the order of 99%, in a fluid bed reactor, with selectivities to methyl glyoxylate in the range of 27% to 49%.

Initial studies with the use of the catalyst of the invention in a fixed bed reactor indicated that while similarly high yields could be obtained the Opportunity for increased selectivity was also available.

A typical preparation of catalyst used in the fixed bed reactor experiments is illustrated in Example B.

EXAMPLE B

Ferric nitrate nonahydrate (229.5 g) was dissolved in distilled water (40ml) to produce a dark brown solution. 85% phosphoric acid (68g) was added to the solution resulting in a pink colored clear solution with a volume of 235ml. An aliquot of the above solution (60g, about 42ml) was added in small portions to alumina support material (112g) with continuous shaking. The support material was Norton Company SA5205, which is an α-alumina material in the form of 3/16 inch (4.7 mm) spheres with a surface area of about 0.05 $m^2/g$. Once all the required solution was added, the resultant mixture was Placed under vacuum to remove water at about 40° C.. The impregnated alumina was then transferred to a dish and dried at 110° C. overnight. The dried material was calcined at 400° C. for 3 hours, and then 800° C. for 3 hours. The material obtained had a slight yellow color with light pink spots on some of the catalyst particles.

Utilizing the apparatus depicted in FIG. 1, a series of experiments, as described below, were performed in which one or more of glycolate concentration, nitrogen addition, catalyst level, catalyst support, reactor operating temperature, $O_2$/glycolate ratio, and addition of alkanol to the feed were studied.

EXAMPLE 1

Fresh catalyst (109 grams), prepared as in Example B and containing 12% ferric phosphate, was placed in the reactor of FIG. 1. For ease of description ferric phosphate on alumina is sometimes referred to as the catalyst even though it is recognized that the active catalyst is the phosphate. After the temperature of reactor 7 (catalyst bed) was raised to 270° C., a mixture of vaporized methyl glycolate, air and nitrogen was fed to the reactor which was maintained at 270° C.. Vaporizer 4 was maintained at a temperature of about 165° C.. The flow rates were: glycolate ester-1.00 gms/min.; nitrogen-944 SCCM; air-2000 SCCM. Glycolate ester concentration was maintained at 7.80% by volume, the $O_2$/glycolate mole ratio was 1.60 and the $O_2$ concentration in the feed was 13.15% by volume. Product was recovered in vessel 9 after passing through chilled condensers 8. Analysis of the product, from samples taken after about two hours of steady operation, showed that product recovery was 99.60%, glycolate ester conversion was 28.71% at a glyoxylate selectivity of 77.50%.

EXAMPLE 2

The procedure of Example 1 was followed but the various rates were changed to provide a glycolate ester feed rate of 2.02 gm./min. with a corresponding increase in air and nitrogen flows to maintain an $O_2$/glycolate mole ratio of 0.84 and glycolate concentration of 10.05%. (Air flow was 2500 SCCM and nitrogen flow was 2000 SCCM). The reactor temperature was 298° C., $O_2$ concentration was 8.40%. The catalyst (109 grams), which was not fresh, contained 12% $Fe_3PO_4$. Analysis of the product showed that the recovery of product was 103.91% with a conversion of 46.78% and a glyoxylate selectivity of 85.10%.

EXAMPLE 3

The procedure was as in Example 1 except that no nitrogen dilution of the feed was used. Accordingly, with a glycolate feed rate of 3.58 gm./min., glycolate concentration was 13.74% and the $O_2$/glycolate mole ratio was 1.32. To provide these conditions an air flow rate of 5600 SCCM was maintained. The reactor temperature was 375° C. and the $O_2$ concentration was 18.12%. Catalyst concentration and amount was as in Example 1. Under these conditions product recovery was 98.03%, with a conversion of 93.91% and a glyoxylate selectivity of 73.24%.

EXAMPLE 4

The procedure was as described in Example 3. A glycolate feed rate of 2.95 gm./min. and an air flow rate of 15,100 SCCM provided an $O_2$/glycolate mole ratio of 4.30. The $O_2$ concentration was 20.02%, glycolate concentration was 4.60%, and the reactor temperature was 260° C.. Fresh catalyst (122 grams), comprised of 7% $Fe_3PO_4$ on 3/16 inch (4.7 mm) spheres of Carborundum SAHO α-alumina having a surface area of less than 1 $m^2$/gm was employed. Under these conditions product recovery was 71.70%, glycolate conversion was 84.87% and glyoxylate selectivity was 49.57%.

EXAMPLE 5

Following the procedure of Example 1, methyl glycolate was oxidized to methyl glyoxylate using the same catalyst support material as in Example 1 but increasing the ferric phosphate concentration to 14% and employing 145 grams of catalyst. A glycolate feed rate of 3.58 gm./min.,air flow rate of 4500 SCCM and nitrogen flow rate 14,000 SCCM were employed. The $O_2$/glycolate mole ratio was 1.06, oxygen concentration was 4.87% and the percent glycolate in the feed to the reactor was 4.60%. The reactor was maintained at a temperature of 305° C. Under these conditions product recovery was 97.77%. The conversion of glycolate was 35.08% with a selectivity to glyoxylate of 65.19%.

EXAMPLE 6

The procedure was as described in Example 1. The ferric phosphate concentration was 13% by weight. The glycolate feed was maintained at a rate of 2.40 g/min., with an air flow rate of 3000 SCCM and a nitrogen flow rate of 10,000 SCCM. In addition, methanol was added to the glycolate feed in an amount of 10% by weight. The $O_2$/glycolate ratio was maintained at 1.08 with a glycolate concentration in the feed of 5.10% and the reactor temperature was 290° C.. Under these conditions the product recovery was 105.75%, conversion was 85.73% and selectivity to methyl glyoxylate was 93.87%.

The results of additional experiments following the general procedure of Example 1 are presented in Table 2 below.

EXAMPLE 19

The procedure of Example 18 was followed except that nitrogen was used as a diluent gas. The methyl glycolate feed, containing 10% methanol by weight, was at a rate of 7.80 gm./min., oxygen flow was 10,000 SCCH and nitrogen flow was 30,000 SCCM. With these flows the $O_2$/glycolate mole ratio was 1.08, the $O_2$ concentration was 5.00% and the glycolate concentration was 4.63%. The catalyst concentration was 6% on the same support. The reactor temperature was maintained at 295° C. Under these conditions the product recovery was 103%, conversion to glyoxylate was 56.93% and the selectivity was 92.76%. Acidic by-products were measured at 1.51% by weight.

EXAMPLE 20

The procedure followed was as described in Example 19. However, in addition to the catalyst of this invention, the reactor was packed with about a 6-8 inches

TABLE 2

Methyl Glycolate Oxidation in a Fixed Bed Reactor

| | Exp. No. | | | | | | | | | | |
|---|---|---|---|---|---|---|---|---|---|---|---|
| | 7[a] | 8 | 9 | 10 | 11 | 12 | 13 | 14 | 15 | 16 | 17 |
| Catalyst Amount (g) | 122 | 122 | 135 | 125 | 125 | 125 | 125 | 125 | 125 | 123 | 92 |
| $Fe_3PO_4$ on Support (wt. %) | 7 | 7 | 16 | 18 | 18 | 18 | 18 | 18 | 18 | 13 | 3 |
| Feed Rate (g/min) | 2.95 | 2.95 | 3.59 | 1.17 | 1.17 | 1.17 | 1.17 | 3.20 | 2.40 | 2.40 | 3.60 |
| Nitrogen Flow (SCCM) | 8000 | 13,200 | 3200 | 4900 | 4900 | 5000 | 4300 | 8700 | 10,000 | 10,000 | 3000 |
| Air Flow (SCCM) | 8000 | 3,000 | 4500 | 1500 | 1500 | 1500 | 2100 | 4000 | 3000 | 3000 | 3000 |
| $O_2$/glyc. Mole Ratio | 2.29 | 0.86 | 1.06 | 1.08 | 1.08 | 1.08 | 1.50 | 1.05 | 1.08 | 1.08 | 1.05 |
| $O_2$ in the Mixture (vol. %) | 10.04 | 3.72 | 11.00 | 4.70 | 5.10 | 5.10 | 6.58 | 6.22 | 5.10 | 5.10 | 9.50 |
| Glycolate in the Mixture (vol. %) | 4.40 | 4.33 | 10.39 | 4.35 | 4.40 | 4.40 | 4.47 | 5.98 | 4.40 | 4.40 | 9.10 |
| Wt. Hrly. Space Velocity | 1.45 | 1.45 | 1.70 | 0.56 | 0.56 | 0.56 | 0.56 | 1.54 | 1.15 | 1.15 | 1.57 |
| Contact Time (sec) | 0.22 | 0.22 | 0.43 | 0.52 | 0.49 | 0.49 | 0.49 | 0.25 | 0.28 | 0.28 | 0.91 |
| Vaporizer Temp (°C.) | 150 | 150 | 150 | 150 | 150 | 150 | 150 | 150 | 150 | 150 | 150 |
| Reactor Temp (°C.) | 270 | 260 | 400 | 320 | 350 | 350 | 350 | 340 | 290 | 290 | 300 |
| Product Recovery (wt. %) | 98.50 | 100.76 | 97.22 | 106.52 | 107.18 | 106.86 | 102.57 | 106.08 | 104.75 | 105.75 | 104.94 |
| Conversion (wt. %) | 77.71 | 55.64 | 84.50 | 66.96 | 88.48 | 91.43 | 96.49 | 63.84 | 107.13 | 68.73 | 62.40 |
| | 90.28 | 61.84 | | | | | | | | | |
| Selectivity (wt. %) | 65.24 | 76.37 | 60.46 | 83.42 | 84.36 | 82.03 | 75.25 | 82.49 | 88.34 | 85.87 | 81.37 |
| | 86.23 | 85.33 | | | | 0.55 | | | | | |
| Pressure Drop (PSI) | 0.50 | 0.75 | 0.50 | 0.20 | 0.15 | 0.15 | 0.20 | 0.30 | 0.20 | 0.25 | 0.10 |

[a]Catalyst-Carborundum SAHO low surface area-3/16 inch (7.4 mm) spheres.

Experiments were also conducted in which reactor 7 was replaced by a reactor having a diameter of 1 inch (25.4 mm and a length of 48 inches (122 mm). To handle this increased reactor capacity the size of the vaporizer was increased to 1/2 inch (12.7 mm) diameter tubing 8 inches (203 mm) long. These experiments are described below.

EXAMPLE 18

Again following the procedure described in Example 1, methyl glycolate was oxidized to methyl glyoxylate In this experiment the concentration of ferric phosphate was 6% deposited on 3/16 inch (4.7 mm) spheres of α-alumina. The total charge of catalyst was 401 grams. The glycolate feed rate was 5.49 gm./min. and the air flow was 39,000 SCCM. Nitrogen was not employed. These flows provided an oxygen content in the feed of 20.30%, a glycolate concentration of 3.38% and an $O_2$/glycolate mole ratio of 6.00. The temperature of the reactor was maintained at 295° C.. Under these conditions the recovery of product was 108%, conversion was 71.29% and selectivity was 85.04%.

(about 152-203 mm) of silver catalyst in the form of silver needles (as described elsewhere herein) arranged so that the feed to the reactor first contacts the catalyst of the invention, which contained 6% ferric phosphate. The glycolate feed rate was 9.82 g/min. with an air flow rate of 12,500 SCCM and a nitrogen flow rate of 37,800 SCCM. The reactor temperature was 252° C. and the $O_2$/glycolate mole ratio was 1.10. The glycolate feed concentration was 5.0%. Under these conditions product recovery was 102.24%, conversion to glyoxylate was 52.19% and the selectivity was 84.69%. The acid content of the product was measured at 0.99% by weight.

The results of other experiments in the longer reactor are summarized in Table 3, below.

TABLE 3

| | Exp. No. | | | |
|---|---|---|---|---|
| | 21[b] | 22 | 23 | 24[c] |
| Catalyst Amount (g) | 311 | 401 | 401 | 401 |
| $FePO_4$ on Support (wt. %) | 6 | 6 | 6 | 6 |
| Feed Rate (g/min) | 8.40 | 5.49 | 7.80 | 7.80 |
| MeOH in feed (wt %) | — | 10 | — | 20 |
| Nitrogen Flow (SCCM) | — | — | 30,000 | 30,000 |
| Air Flow (SCCH) | 38,000 | 39,000 | 10,000 | 10,000 |
| $O_2$/glyc. Mole Ratio | 3.82 | 6.00 | 1.08 | 1.08 |

TABLE 3-continued

|  | Exp. No. | | | |
| --- | --- | --- | --- | --- |
|  | 21[b] | 22 | 23 | 24[c] |
| O₂ in the Mixture (vol. %) | 20.00 | 20.30 | 5.00 | 5.00 |
| Glycolate in the Mixture (vol. %) | 4.30 | 3.38 | 4.63 | 4.63 |
| Wt. Hrly. Space velocity | 1.62 | 0.82 | 1.17 | 1.17 |
| Contact Time (sec) | 0.22 | 0.27 | 0.26 | 0.26 |
| Vaporizer Temp (°C.) | 180 | 150 | 150 | 150 |
| Reactor Temp (°C.) | 300 | 295 | 300 | 270 |
| Product Recovery (wt. %) | 89.30 | 103 | 102.50 | 102 |
| Conversion (wt. %) | 91.07 | 76.48 | 51.53 | 51.00 |
| Selectivity (wt. %) | 63.56 | 91.60 | 85.97 | 91.00 |
| Pressure Drop (PSI) | 0.70 | 1.40 | 1.70 | 1.90 |

[b]Fresh cat. with 0.5% potassium nitrate added. 1.50% Acids in the product
[c]1.30% Acids in the product Analysis of the crude reaction products from the various experiments was done on a Hewlett-Packard, Model 5710A, gas chromatograph. A 10×⅛Δ Nickel 200 column, packed with Tenax-GC, 80/100 with a He flow of approximately 12 ml/minute was used. The GC was held at 100° C. starting temperature for 4 minutes, then raised to 270° C. at 8°/minute, and then held for an additional 2 minutes. By this procedure it is possible to identify water, alkanol, alkyl formate, alkyl glyoxylate, alkyl glycolate, alkyl alkyloxyacetate, alkyl, and alkyl tartronate. Response factors for all of these materials with the exception of alkyl and alkyl tartronate were obtained using a standard of tetraethylene glycol dimethyl ether. Response factors for alkyl and tartronate were assumed to be 1.00.

While the process of this invention has been illustrated using methyl glycolate, other lower alkyl glycolates can also be used to prepare corresponding lower alkyl glyoxylates. Lower alkyl glycolates is intended to include methyl glycolate, ethyl glycolate, propyl and isopropyl glycolate and the butyl glycolates; that is, n-butyl, iso-butyl, and tert-butyl glycolates.

In view of the above, it will be seen that the several objects of the invention are achieved and other advantageous results attained.

As various changes could be made in the above processes and compositions without departing from the scope of the invention, it is intended that all matter contained in the above description or shown in the accompanying drawings shall be interpreted as illustrative and not in a limiting sense.

What is claimed is:

1. A catalyst composition consisting essentially of the calcined residue of ferric phosphate on support material selected from the group consisting of alumina and silica-alumina wherein the surface area of the support material is between about 0.02 m²/g and 45 m²/g.

2. A catalyst composition of claim 1 wherein the surface area of said alumina support material is between about 0.02 m²/g and about 5 m²/g and the concentration of ferric phosphate on said support material is about 6-18% by weight.

3. A catalyst composition of any one of claims 1-2 wherein the alumina support material is in the alpha-alumina form and contains up to about 20% by weight silica.

4. A method for preparing a ferric phosphate on alumina oxidation catalyst comprising:
   (a) preparing an aqueous solution of ferric ions and phosphate ions;
   (b) mixing said aqueous solution with an alumina support material having a surface area of about 0.02 m²/g; and
   (c) calcining said support material at about 400°-800° C.

5. A method of claim 4 wherein the alumina support material is in the α-alumina form and contains less than about 20% by weight silica and the amount of said aqueous solution is such as to provide about 1-20% by weight of ferric phosphate on said support material.

6. A method of claim 5 wherein the alumina support material is dried after being mixed with said solution before calcining.

7. A method of claim 6 wherein the silica content of said support material is less than about 12% by weight.

8. A method of claim 4 wherein the alumina support material is in the α-alumina form and contains up to about 20% silica and the concentration of ferric phosphate on said support material is from about 6-18% by weight 9. A method of claim 7 wherein the concentration of ferric phosphate on said support material is from about 6-18% by weight.

* * * * *